United States Patent
Kleizo et al.

(10) Patent No.: US 10,357,064 B1
(45) Date of Patent: Jul. 23, 2019

(54) PERSONAL VAPORIZER AND AROMATHERAPY DIFFUSER

(71) Applicant: BONGO MANUFACTURING, LLC, Sanford, FL (US)

(72) Inventors: Matthew R. Kleizo, Longwood, FL (US); Christoffer Lee Clemens, Henderson, NV (US); James Youwon So, Los Angeles, CA (US)

(73) Assignee: BONGO MANUFACTURING, LLC, Sanford, FL (US)

( * ) Notice: Subject to any disclaimer, the term of this patent is extended or adjusted under 35 U.S.C. 154(b) by 0 days.

(21) Appl. No.: 16/299,489

(22) Filed: Mar. 12, 2019

(51) Int. Cl.
*A24F 47/00* (2006.01)
*A61M 21/02* (2006.01)
*A61M 11/04* (2006.01)
*H05B 3/44* (2006.01)
*A61M 21/00* (2006.01)

(52) U.S. Cl.
CPC ......... *A24F 47/008* (2013.01); *A61M 11/042* (2014.02); *A61M 21/02* (2013.01); *H05B 3/44* (2013.01); *A61M 2021/0016* (2013.01); *A61M 2205/0211* (2013.01); *A61M 2205/3653* (2013.01)

(58) Field of Classification Search
CPC ............................ A24F 47/008; A61M 11/042
See application file for complete search history.

(56) References Cited

U.S. PATENT DOCUMENTS

| | | | |
|---|---|---|---|
| 8,550,068 B2 | 10/2013 | Terry et al. | |
| 9,497,994 B2 | 11/2016 | Liu | |
| 9,854,848 B1 | 1/2018 | Servutas | |
| 2016/0227837 A1* | 8/2016 | Hammel | A24F 47/008 |
| 2016/0262452 A1* | 9/2016 | Zhu | A24F 47/008 |
| 2017/0079332 A1* | 3/2017 | Li | A24F 47/008 |
| 2017/0112192 A1* | 4/2017 | Shan | A24F 47/008 |
| 2018/0279683 A1* | 10/2018 | Qiu | A24F 47/008 |
| 2018/0303166 A1* | 10/2018 | Qiu | A24F 47/00 |
| 2018/0317556 A1* | 11/2018 | Chen | A24F 47/008 |
| 2019/0116884 A1* | 4/2019 | Conley | A24F 47/008 |

* cited by examiner

*Primary Examiner* — Eric Yaary
(74) *Attorney, Agent, or Firm* — Allen, Dyer, Doppelt + Gilchrist, P.A.

(57) ABSTRACT

A vaporizer and aromatherapy diffuser includes a base and angled tank floor. A lower end of a coil support tube is configured as a connector to a battery housing and an upper end forms a central air passage. A second air slot communicates with a first air slot in the base. A heating coil within the coil support tube is adjacent at least one opening, and a porous wick surrounds the heating coil. A tank cap forms a sealed fluid tank for holding vaping fluid. When suction is applied, air is drawn upward into the coil support tube through the porous wick and draws botanical extract contained within the sealed fluid tank through the coil support tube into the porous wick for vaporization. The tank cap has a fill hole. A drop tip is secured onto the tank cap and covers the plug to prevent refill.

27 Claims, 13 Drawing Sheets

US 10,357,064 B1

PERSONAL VAPORIZER AND AROMATHERAPY DIFFUSER

FIELD OF THE INVENTION

This invention relates to personal vaporizers, and more particularly, this invention relates to a personal vaporizer that may be used as a vaping device or aromatherapy diffuser to deliver a vaping fluid or botanical extract for vaping and/or diffusion.

BACKGROUND OF THE INVENTION

Personal vaporizers, such as electronic cigarettes, vaping or vape devices, and commercially known atomizers, cartomizers and clearomizers, have become very popular in the last few years. Many of these devices operate as a battery-powered vaporizer that includes a mouth piece, and in one design, a rebuildable device or deck, a juice or e-liquid that is vaporized, and a heating element or similar atomizer, which is activated by a switch. The heating element is typically a heating coil and heats and vaporizes the vaping juice. A wicking material helps draw the juice or liquid onto the coil such as from a well or fluid tank that holds the juice. In some devices, the user manually depresses a button on the side of the housing or at the end or bottom of the device to close the switch and actuate a contact button or "firing pin" or other contact device to complete the circuit between the battery and the atomizer.

The vaporizer designs currently in use vary and recent design modifications include mechanical "mods," for example, that may have a rebuildable atomizer deck that allows a user to assemble or "build" the wick and coil themselves, instead of using off-the-shelf atomizer "heads." These types of devices are often termed a rebuildable dripping atomizer (RDA), or sometimes referred to as a "dripper." Experienced users of these designs enjoy building their atomizers because they can choose a specific configuration and electrical resistance of their coil, and thus, pick their flavor and the amount of aerosolized vapor produced by the electronic cigarette.

There are other devices commercially known as atomizers, cartomizers and clearomizers that may also screw on a battery housing or power supply to deliver the E-juice or E-liquid as a vaping fluid to be atomized in a vapor form. Those skilled in the art recognize atomizers as typically having a small capacity for those that prefer dripping and allow easy switching between different flavors of juices. Many have a heating coil on the bottom and a metal mesh on the top of the coil, but others may use as silica wick. The cartomizers, on the other hand, sometimes have a polyfill wrapped around a heating coil that soaks the vaping fluid and allows for a longer vape time compared to an atomizer. They sometimes have a larger cylindrical tank. The clearomizers are usually cylindrical and have clear polycarbonate plastic or Pyrex glass tank as a fluid tank so that the user may see the level of vaping fluid or E-juice inside the clearomizer as the vaping device. The vapor fluid is delivered to a heating coil by the silica wick. Some of these designs may have a heating coil with longer wicks and others have a bottom placed heating coil with short wicks that allow for easier wick saturation. Some models are rebuildable with replaceable coils.

In another design variation, different vaping devices may be regulated or unregulated "mods." The unregulated mods do not contain a circuit board for regulating power flow through the device. An example is a mechanical mod, or a series of parallel box mods without a display or variable voltage and wattage, and sometimes semi-mechanical mods. A regulated mod, on the other hand, contains a circuit board or a chip or processor to regulate the current and sometimes voltage. Devices that have a variable voltage or wattage setting are considered regulated devices. Regulated devices typically have increased safety, ease of use, digital display, and other benefits.

With the rise of many users becoming more health conscious and desiring medicinal or botanical extracts such as cannabinoids, there is a need for improved vaping devices as vaporizers that can deliver botanical extracts in an efficient, safe manner, and even as single use, disposable devices, which would be especially useful with medicinal products, cannabinoids and other botanical extracts. There are design considerations that must be taken into consideration since the vaping fluids from a botanical extract, such as derived from *cannabis*, is very thick or viscous compared to a traditional vaping fluid. These thicker vaping fluids from botanical extracts, for example, do not flow as easily as a traditional vaping fluid. If a thicker vaping fluid is used, it often settles in juice tanks or fluid reservoirs having planar configured bottom floors or surfaces and tends to accumulate against 90° corners, making the last remnants of the juice inaccessible for use. With very expensive botanical extracts as a vaping fluid, such as a cannabinoid, it is necessary to use the entire stored botanical extract, i.e., every drop contained in the reservoir, since there is such a high cost of producing that specialized vaping mix.

Another drawback of many conventional vaping devices as vaporizers is when they are used with botanical extracts, those extracts may be subject to oxidation. Because almost all vape devices are easily refillable, if a very expensive botanical extract is stored within the juice tank or reservoir for a period of time, it may oxidize over time and be unusable. Also, a botanical extract as a vaping fluid often requires higher temperatures to vaporize the extract, as compared to the more traditional vaping fluids. Additionally, because many vaping devices as vaporizers are refillable, they can be messy to refill, and often there is some spillage of the vaping fluid, which is impractical if the vaping fluid is formed from an expensive botanical extract such as a cannabinoid. Thus, because most known vaping devices as vaporizers are refillable and not sealed against oxidation, the use of such devices could create problems where an expensive botanical extract forming the vaping fluid could be subject to oxidation or spilled, and thus, wasted.

SUMMARY OF THE INVENTION

This summary is provided to introduce a selection of concepts that are further described below in the Detailed Description. This summary is not intended to identify key or essential features of the claimed subject matter, nor is it intended to be used as an aid in limiting the scope of the claimed subject matter.

A vaporizer and aromatherapy diffuser includes a base having an outer surface and conical upper surface defining an angled tank floor. The base includes a central orifice and at least one first air slot extending from the outer surface into the central orifice below the angled tank floor. A coil support tube is received within the central orifice of the base and has a lower end extending below the base and configured as a connector to connect to a battery housing. A contact pin is carried at the connector. An upper end extends above the base and forms a central air passage. The coil support tube has at least one opening formed in the side adjacent the angled tank floor and at least a second air slot below the angled tank floor and communicating with the at least first air slot in the base.

A heating coil is received within the coil support tube adjacent the at least one opening, and a porous wick surrounds the heating coil. A lead connects the heating coil and the contact pin. A tank cap is received over the base and sealed thereto and encloses the coil support tube as a shell forming a sealed fluid tank for holding vaping fluid. The tank cap has at least one third air slot formed below the angled tank floor and communicates with the at least one first and second air slots.

The tank cap has an upper surface and a central vapor outlet having an upper end extending from the upper surface and a lower end that connects to the upper end of the coil support tube in sealed engagement. Upon suction applied at the upper end of the outlet, air is drawn through the at least first, second and third air slots upward into the coil support tube through the porous wick and drawing vaping fluid contained within the sealed fluid tank through the at least one opening in the coil support tube into the porous wick for vaporization by the heating coil and discharge from the outlet within the tank cap. The tank cap has a fill hole within the upper surface to allow filling of the sealed fluid tank with a vaping fluid and a plug secured into the fill hole. A drip tip is secured onto the tank cap and covers the plug.

In an example, the vaping fluid comprises a botanical extract. The angled tank floor may be configured to assist gravity feeding of the vaping fluid from the sealed tank to the porous wick and adjacent the heating coil to transfer heat to the vaping fluid. The drip tip may be secured onto the tank cap and covers the plug secured within the fill hole to prevent refill of the sealed fluid tank with a vaping fluid. The heating coil may comprise a ceramic heating coil. The heating coil may comprise a mesh heating coil. The porous wick may comprise a cotton wick.

In another example, the sealed fluid tank may have a capacity of 0.3 milliliters to 8.0 milliliters, and the heating coil may have a 0.11 ohm to 2.1 ohm resistance. The cylindrical base, coil support tube, tank cap and drip tip are formed of a plastic material. The connector at the lower end of the coil support tube may comprise a 510 connector to connect to a battery housing of a vaping mod device. An O-ring may be positioned between the base and tank cap to prevent leakage of vaping fluid therebetween. An O-ring may be positioned between the base and coil support tube to prevent leakage of vaping fluid therebetween. The sealed fluid tank when filled with a vaping fluid may create a low pressure air pocket that retains the vaping fluid within the sealed fluid tank until a user draws air through the central passage formed by the upper end of the coil support tube and outlet of the tank cap to create a lower air pressure in the central passage than in the sealed fluid tank and allow vaping fluid to flow into the porous wick and central air passage. The drip tip may comprise permanent securement onto the tank cap. The tank cap may comprise multiple sections, including an upper section and a lower section, wherein the lower section retains the upper section against the cylindrical base. The coil support tube may include multiple sections, including upper and lower sections.

In yet another example, a single use, disposable vaporizer and aromatherapy diffuser for botanical extracts may include a cylindrical base having an outer surface and conical upper surface defining an angled tank floor. The cylindrical base may have a central orifice and at least one first air slot extending from the outer surface into the central orifice below the angled tank floor. A coil support tube is received within the central orifice of the cylindrical base and has a lower end extending below the cylindrical base and configured as a connector to connect to a battery housing. A contact pin is carried at the connector. An upper end extends above the cylindrical base and forms a central air passage. The coil support tube has at least one opening formed in the side adjacent the angled tank floor and at least a second air slot below the angled tank floor and communicating with the at least first air slot in the cylindrical base.

A 0.11 ohm to 2.1 ohm resistance ceramic or mesh heating coil is received within the coil support tube adjacent the at least one opening. A cylindrical porous wick surrounds the ceramic or mesh heating coil. A lead connects the ceramic or mesh heating coil and the contact pin. A tank cap is received over the cylindrical base and sealed thereto and enclosing the coil support tube as a shell forming a sealed fluid tank having a capacity of 0.3 milliliters to 8.0 milliliters for holding the botanical extract.

The tank cap has at least one third air slot formed below the angled tank floor and communicating with the at least one first and second air slots. The tank cap has an upper surface and a central vapor outlet formed as an outlet tube having an upper end extending from the upper surface and a lower end that connects to the upper end of the coil support tube in sealed engagement. Upon suction applied at the upper end of the outlet tube, air is drawn through the at least first, second and third air slots upward into the coil support tube through the cylindrical porous wick and drawing botanical extract contained within the sealed fluid tank through the at least one opening in the coil support tube into the porous wick for vaporization of the botanical extract by the ceramic or mesh heating coil and discharge from the outlet tube within the tank cap. The tank cap has a fill hole within the upper surface to allow filling of the sealed fluid tank with a botanical extract and a plug secured into the fill hole. A drip tip is secured onto the tank cap and is unremovable and covers the plug secured within the fill hole to prevent removal of the plug and refill of the sealed fluid tank with a botanical extract.

DESCRIPTION OF THE DRAWINGS

Other objects, features and advantages of the present invention will become apparent from the detailed description of the invention, which follows when considered in light of the accompanying drawings in which.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
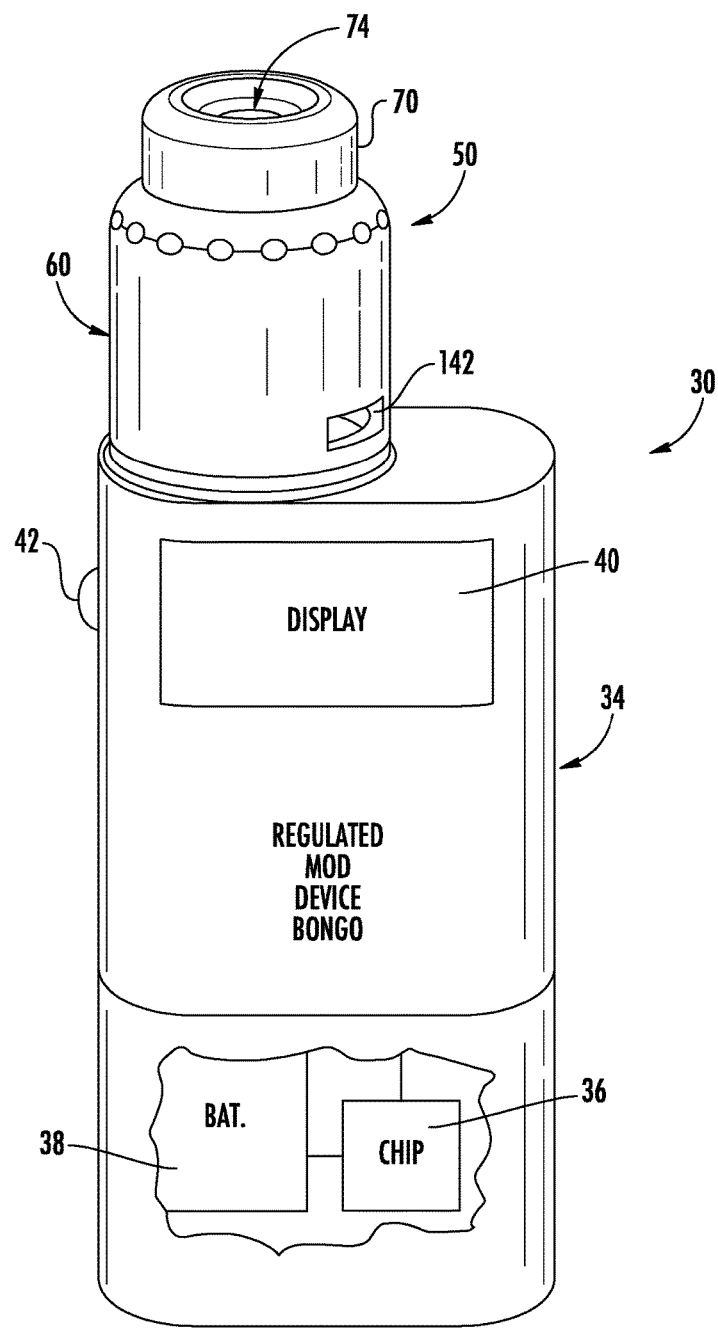
FIG. 1 is an isometric view of the vaporizer and aromatherapy diffuser, also referred to as the vaporizer, connected to a battery housing as a regulated mod device in accordance with a non-limiting example.

Referring now to FIG. 1, there is illustrated a vaporizer and aromatherapy diffuser assembly, which also may be referred to as a "mod" device generally at 30, which includes two components as the battery housing, also referred to as the "mod" housing and generally shown at 34, and the vaporizer and aromatherapy diffuser connected to the battery housing 34 and indicated generally at 50, and hereinafter also referred to generally as the vaporizer. The vaporizer 50 may also be termed a vaping device and used for personal vaping, but also diffusion of vaping fluid or botanical extracts, for example, without a user drawing air through the device as with conventional vaping devices, but by allowing vaping fluid or botanical extract to diffuse outward from the device when a heating coil is activated. Several essential oils could be diffused to create a customer aroma with multiple therapeutic benefits in an example. Essential oils could be diffused as a fine vapor throughout the air so it can be absorbed gently in the body.

The battery housing 34 is configured as a box mod and with the vaporizer 50 connected thereto is a regulated device, with the battery housing containing a circuit board or chip illustrated at 36, within the broken side wall image section, and at least one internal battery 38 contained within the battery housing for providing power to the chip or circuit board and the vaporizer 50. The mod housing 34 may include a display 40 and a switch 42 that is operative when depressed, for example, to complete the electrical circuit to operate the vaporizer 50. This regulated device will work with the vaporizer 50 at a general wattage of about 10 watts to 100 watts, for example, and the display 40 could be interactive as a user interface to regulate the wattage and sometimes voltage. The regulated device is a safer device than unregulated devices, and the regulated device typically will not cause battery damage, and in worse case scenarios that may occur with unregulated devices, a battery explosion. Also, the regulated device is better suited for operation and vaping with botanical extracts, for example, more viscous and expensive botanical extracts such as derived from *cannabis* products.

Figure 2:
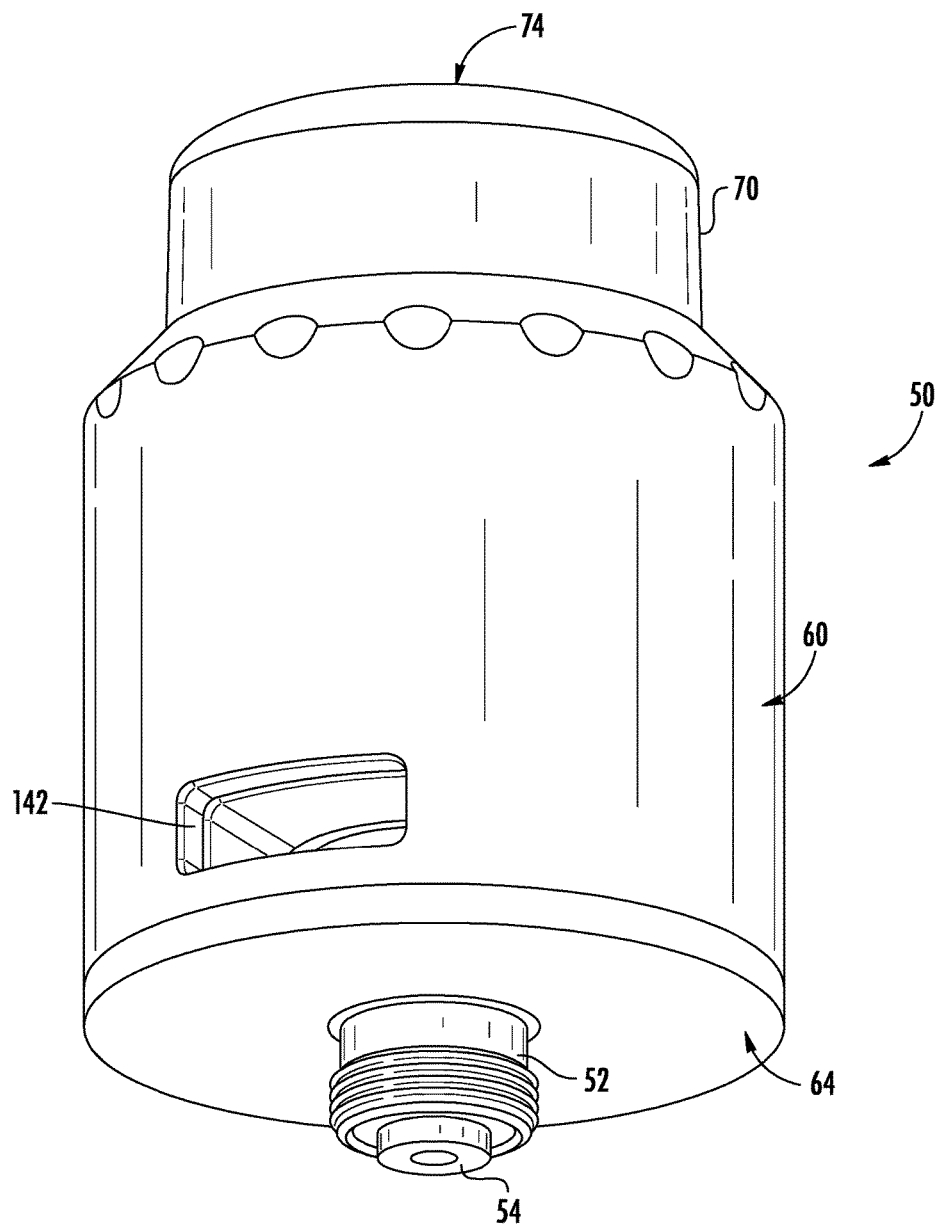
FIG. 2 is an isometric view of the vaporizer of FIG. 1 looking in the direction of the connector.
Figure 3:
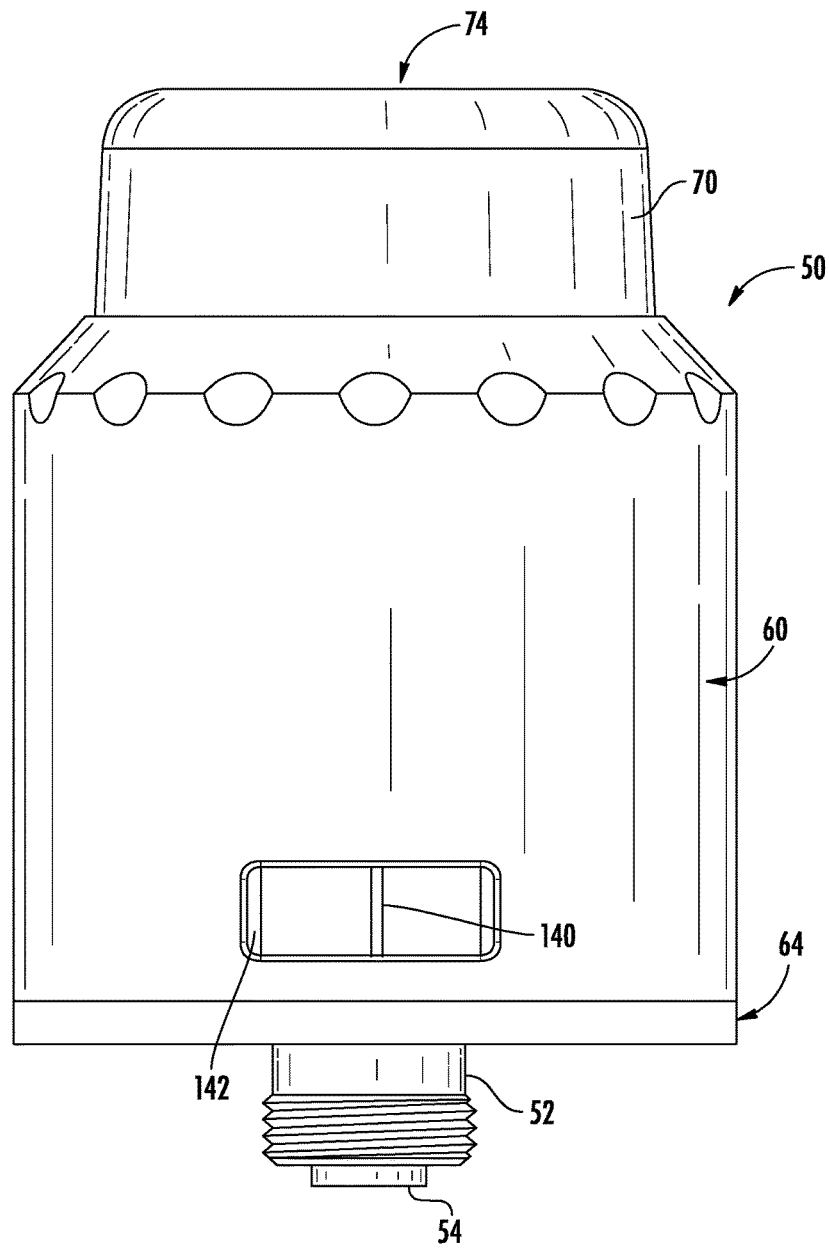
FIG. 3 is a front elevation view of the vaporizer of FIG. 2.

Referring now to FIG. 2, the vaporizer 50 includes a connector 52 and contact pin 54 carried at the connector that connects to the battery housing 34, i.e., the mod housing as shown in FIG. 1. As will be explained in greater detail below, the vaporizer includes a tank cap 60 received over a base 64 that carries a coil support tube 68 having the connector 52 at the end and with the coil support tube 68 shown extending vertically in FIGS. 3 and 13. The tank cap 60 is secured to the base 64, permanently in an example, to form a sealed fluid tank 71 (FIG. 13), such as for botanical extracts.

Although the tank cap 60 is shown as preferably in this example as substantially cylindrically configured, it should be understood that it could be any configuration or shape, such as oval, rectangular, square, octagonal and other shapes. The base 64 is preferably circular configured as illustrated, but also could be other shapes depending on the design options of those skilled in the art. For purposes of description, the base 64 will be referred to hereinafter as the circular base as illustrated, but with the understanding it could be any shape.

Figure 4:
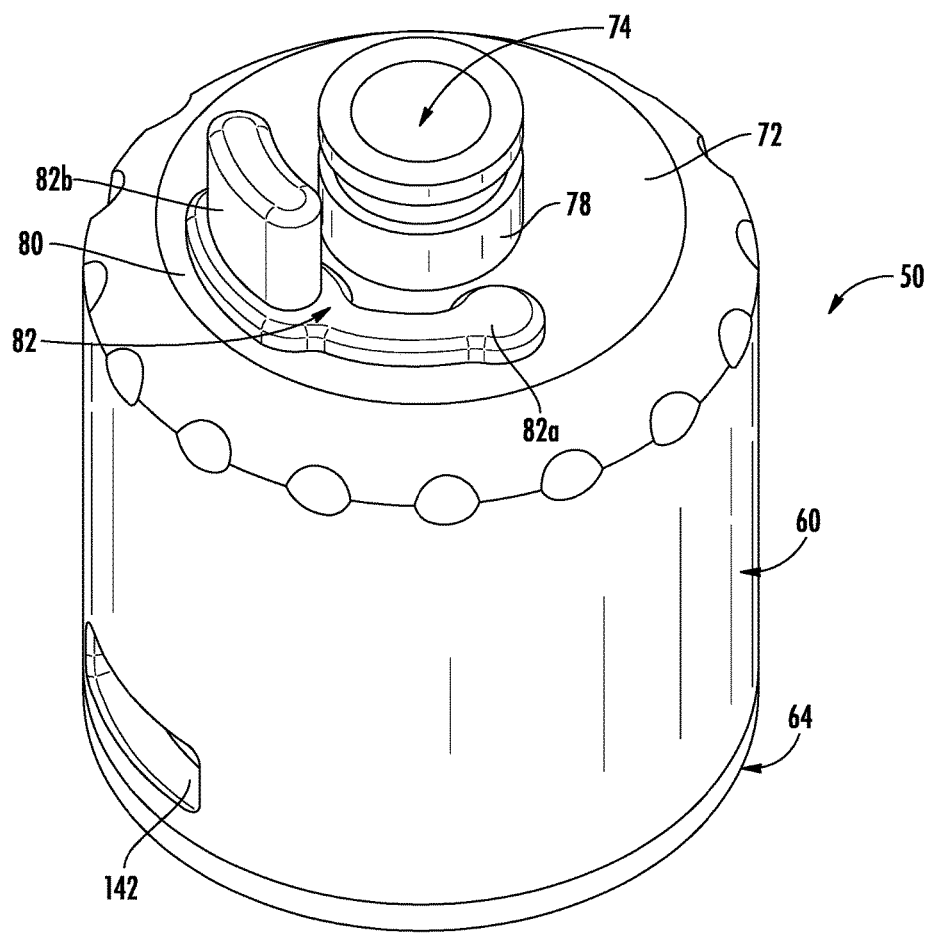
FIG. 4 is an isometric view of the vaporizer of FIG. 1 with the drip tip removed, showing the plug secured in the fill hole and showing the upper end of the outlet.

A drip tip 70 is secured onto the upper surface 72 of the tank cap, and is removed in the view of FIG. 4, which shows the top portion of the tank cap 60 as a substantially planar upper surface 72 and having a central vapor outlet 74, which in the preferred embodiment as part of an outlet 78 in this example, and having an upper end extending from the upper surface 72 of the tank cap 60. In the illustrated example, the outlet 78 is formed as an outlet tube, but could be many different shapes, such as rectangular, square, oval, circular, octagonal or other shapes. For purposes of description, the outlet 78 is referred to herein as the outlet tube. The drip tip 70 is illustrated as circular, but it also could be many different shapes, including square, rectangular, oval, octagonal or other shape. One configuration that may be preferred by those skilled in the art besides the circular configuration is a "whistle tip" configuration, such as evident on some e-cigarette style devices.

Figure 13:
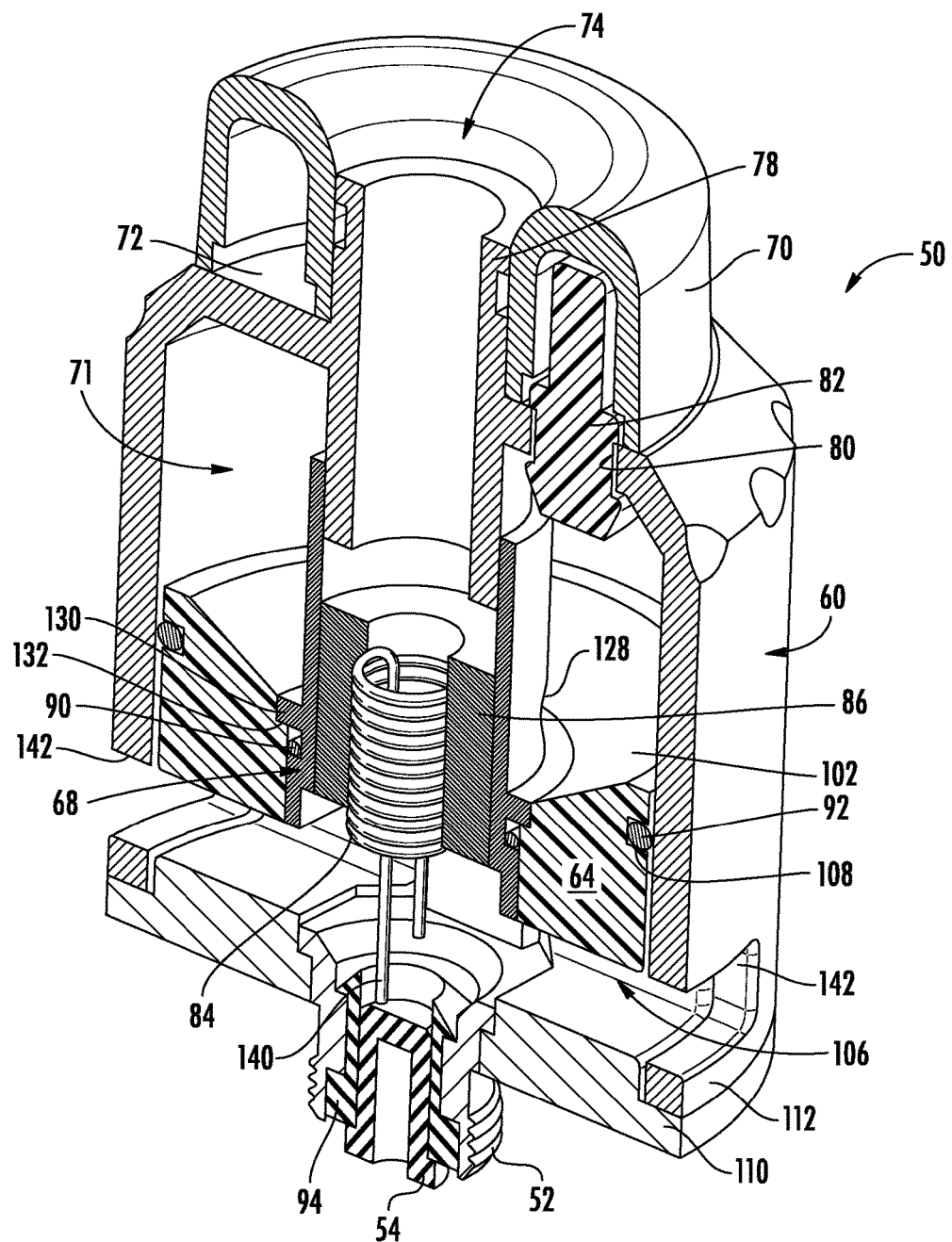
FIG. 13 is an isometric sectional view of the vaporizer of FIG. 1.
Figure 14:
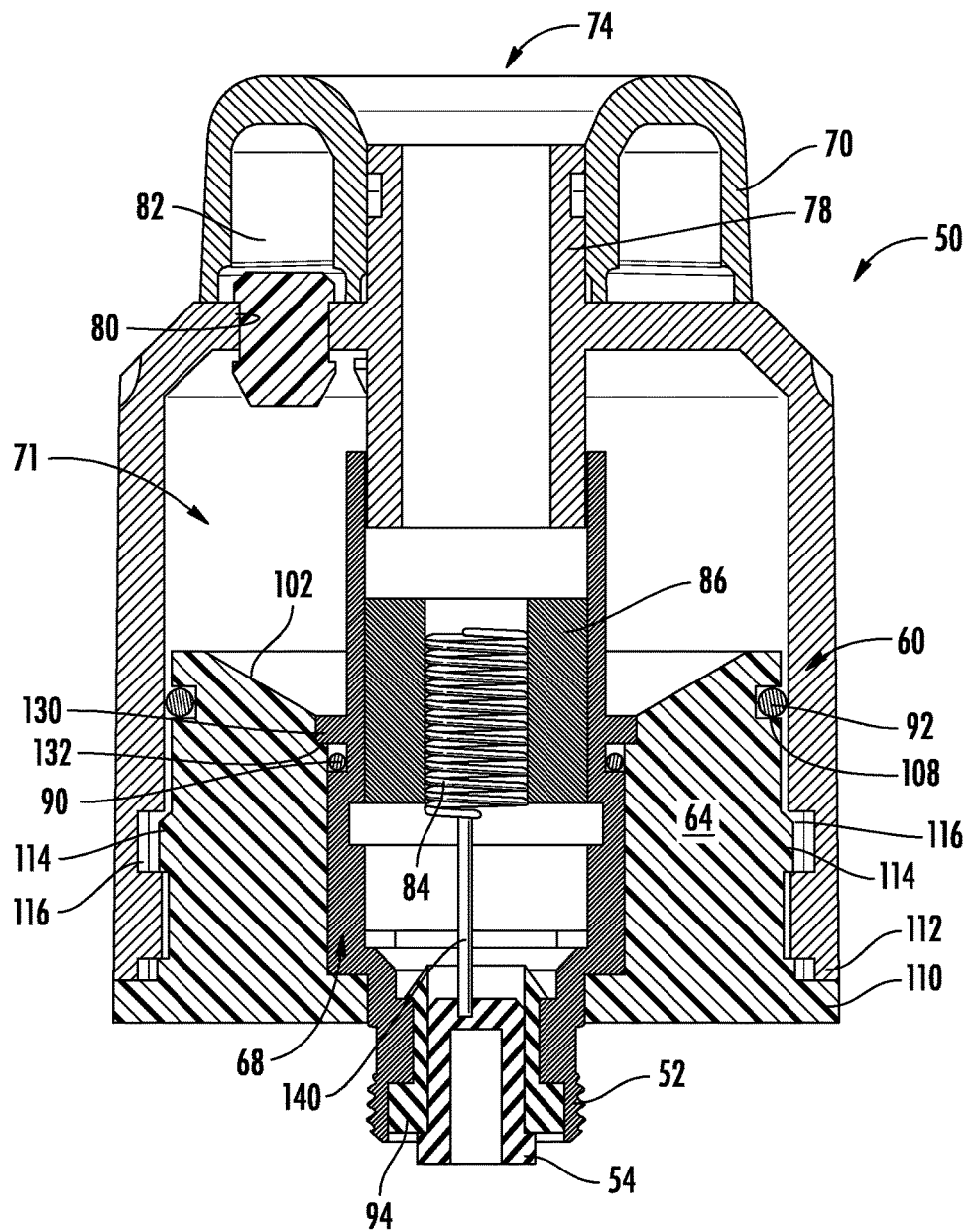
FIG. 14 is a front sectional view of the vaporizer shown in FIG. 1.
Figure 15:
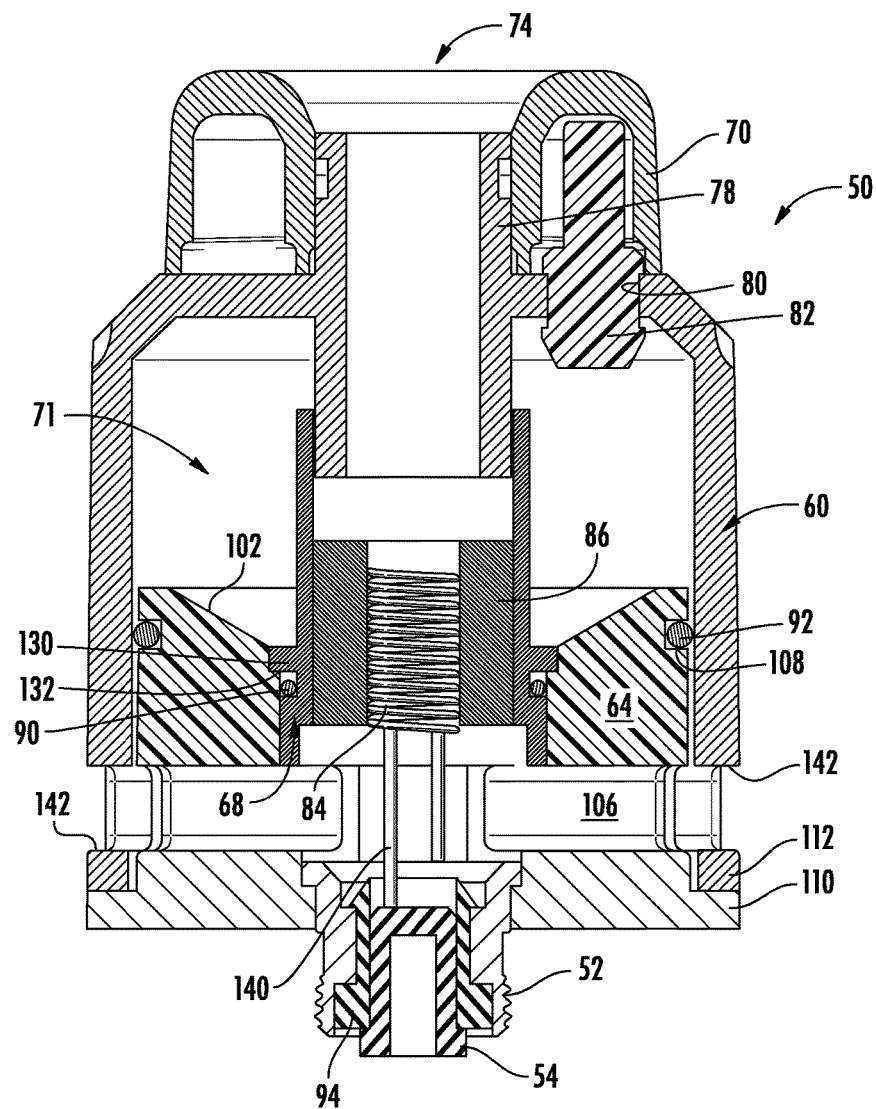
FIG. 15 is a side sectional view of the vaporizer shown in FIG. 1.

The tank cap 60 includes a fill hole 80 and a plug 82 secured into the fill hole as better shown in FIGS. 13-15. In this embodiment, the sealed fluid tank 71 that is formed by the tank cap 60 and other components as will be explained in greater detail below, is permanently sealed to be a single use and disposable vaporizer 50 for use with botanical extracts. The drip tip 70 may be secured permanently onto the tank cap 60 and covers the plug 82 in a sealed engagement so that the sealed fluid tank cannot be refilled, to form the single use, disposable vaping and aromatherapy infuser as the vaporizer 50 especially suitable for botanical extracts such as cannabinoids, which are expensive and often better suited for use with a single use and disposable vaporizer. The tank cap 60 includes an air slot that works in conjunction with slots within the vaporizer as explained in greater detail below relative to FIGS. 6-9 and FIGS. 13-15.

Figure 5:
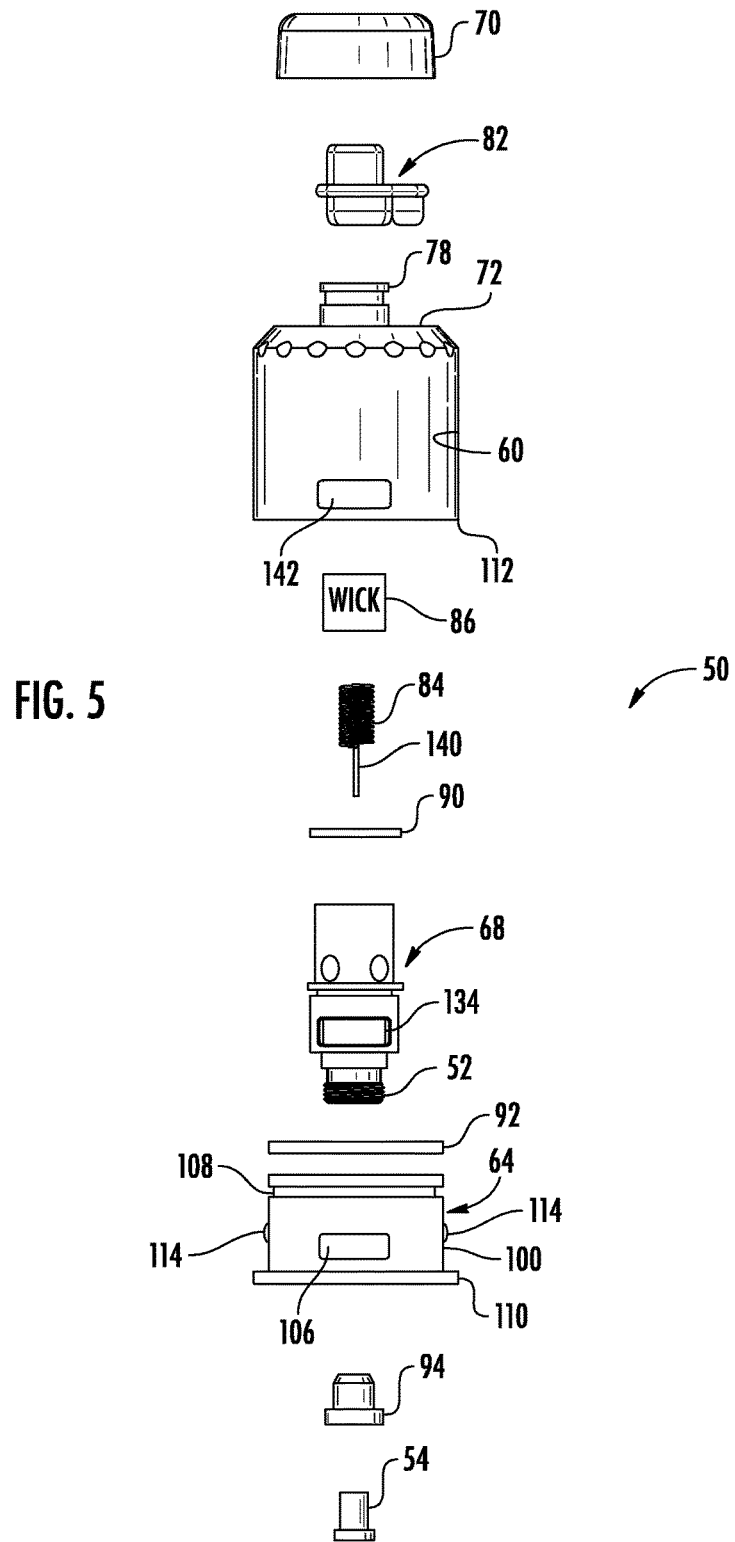
FIG. 5 is an exploded assembly view showing the components of the vaporizer of FIG. 1.
Figure 6:
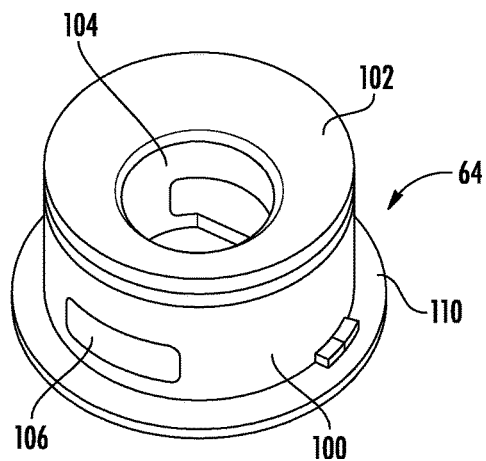
FIG. 6 is an isometric view of the base shown in FIG. 5.
Figure 7:
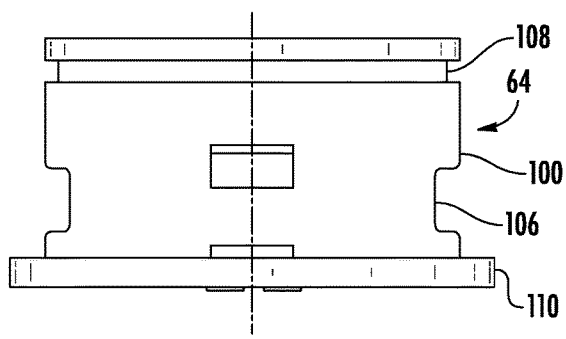
FIG. 7 is a front elevation view of the base shown in FIG. 6.
Figure 8:
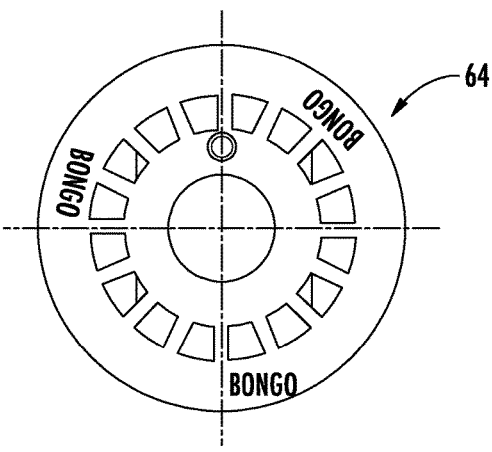
FIG. 8 is a bottom plan view of the base shown in FIG. 6.

Referring now to FIG. 5, an exploded assembly view of an example of the vaporizer 50 of FIG. 1 is illustrated and shows the cylindrical base 64, coil support tube 68, tank cap 60 and drip tip 70 as its four major components. Also illustrated in this example are the heating coil 84 and cylindrical porous wick 86, the plug 82, a first O-ring 90, a second O-ring 92, and the contact pin 54 and a contact pin retainer 94 formed in this example as an insulator. The drip tip 70, tank cap 60, coil support tube 68 and cylindrical base 64 may all be formed from injection molded plastic such as polycarbonate or polyethylene tereththalate (PET and sometimes PETE) and other plastic materials that withstand the degrading and corrosive effects of botanical extracts such as cannabinoids and other vaping fluids and provide heat resistance for the higher heat imparted by the heating coil when it is energized from the battery 38 contained in the housing 34. The plastic components can be made from colored or clear plastic, allowing users to view the internal components if clear plastic, and permitting a user to view better the level of vaping fluid or botanical extract and when it is used or half used, and how much is left in the sealed fluid tank.

The cylindrical base 64 includes an outer surface 100 (FIGS. 6 and 7) and a conical upper surface 102 (FIGS. 6 and 13) defining an angled tank floor of the sealed fluid tank 71. The cylindrical base 64 has a central orifice 104 (FIG. 6) and at least one first air slot 106 extending from the outer surface 100 into the central orifice 104 below the angled tank floor 102 and in this example, two opposing air slots 180° apart forming these first air slots. A circumferential groove 108 (FIG. 7) is formed around the outer surface 100 or periphery near the upper section of the cylindrical base 64 and receives the second O-ring 92 acting as a seal between the cylindrical base and tank cap 60 to help seal the two and prevent vaping fluid or botanical extract leakage. The cylindrical base 64 includes an enlarged circular or peripheral ridge 110 at its bottom section on which the lower peripheral edge 112 of the tank cap 60 rests. Two opposing tabs 114 are formed at the medial section of the cylindrical base 64 on its outer surface 100 to receive in a snap-fit connection, the tank cap (FIG. 14), by having the tabs 114 engage a notch 116 on the inside surface of the tank cap 60.

The bottom of the cylindrical base 64 may include manufacturing logos or indentations or other decorative features (FIG. 8) that may also help stand the vaporizer on its end and retain a grip to the surface. This is advantageous if a user wants to limit their use of the vaporizer for a while, and let it rest on its base. Hot vaping fluid could possible leak from the vaporizer if it is laid on its side in some cases. Also, it may roll if laid on its side depending on configuration. As shown in the front elevation in FIG. 7, the first air slots 106, in an example, may be cut out slightly and formed similar to a notch.

Figure 9:
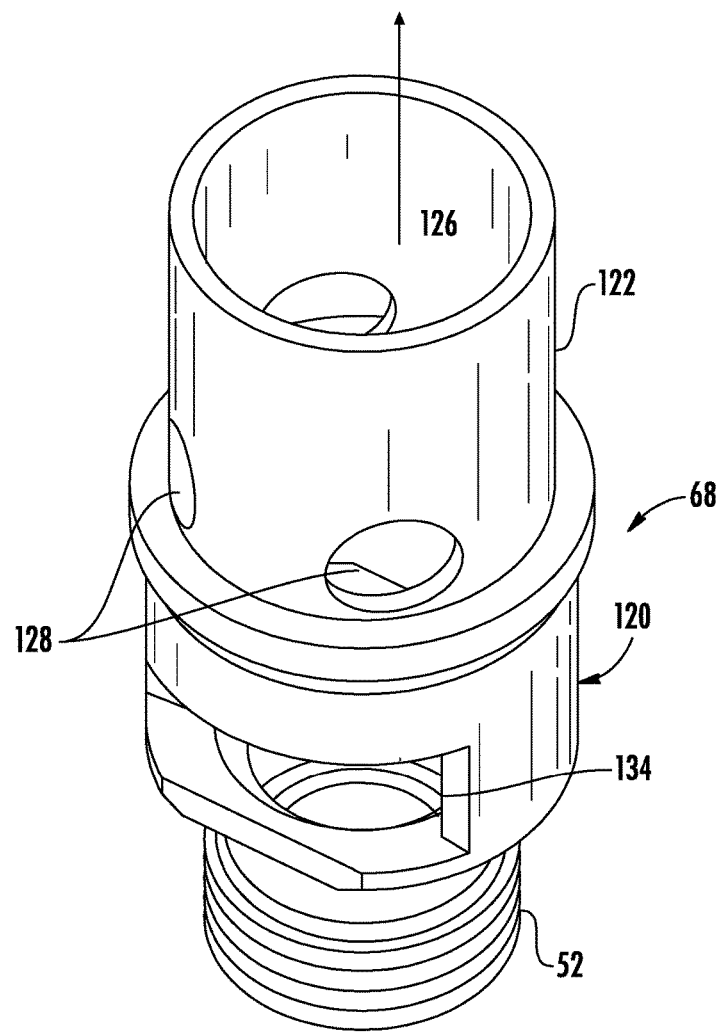
FIG. 9 an isometric view of the coil support tube shown in FIG. 5.

Referring now to FIG. 9, there is illustrated the coil support tube 68 that is configured to be received within the central orifice 104 of the cylindrical base 64. The coil support tube 68 includes a lower end 120 that extends below the cylindrical base 64 when connected thereto and configured as the connector 52 that connects to the battery housing such as the "mod" housing 34 shown in FIG. 1. In this example, the connector 52 is configured as a screw thread connection, and more particularly, a 510 connector that connects to a battery housing of a vaping mod device, which in this example is a regulated mod device 34 such as shown in FIG. 1. A contact pin 54 is carried at the connector 52 (FIG. 13) that contacts a terminal within the battery housing and is helped to be retained in the connector of the coil support tube via a contact pin retainer 94, which is formed as an insulator in this example. The retainer 94 may include a slot that engages an internal shoulder of the coil support tube at the connector.

An upper end 122 of the coil support tube 68 extends above the cylindrical base 64 and forms a central air passage 126 and has at least one opening 128 formed in the side and positioned adjacent the angled tank floor 102 when received in the cylindrical base as best shown in FIG. 13. In the illustrated example, four openings 128 are arranged at 90° from each other in the side of the coil support tube 68. An internal shoulder 130 is formed just below the openings 128 that is configured to rest on an internal ledge 132 formed in the side periphery of the central orifice 104 so that the coil support tube 68 may be secured onto the cylindrical base 64. The lower section of the coil support tube 68 may have an outer diameter that allows an interference fit between the coil support tube and central orifice 104 and cylindrical base 64 so that the coil support tube is retained permanently at the cylindrical base.

The first O-ring 90 is positioned between the cylindrical base 64 and coil support tube 68 to prevent leakage of vaping fluids or other botanical extract therebetween. A second air slot 134 (FIG. 9) is formed below the level of the angled tank floor 102 within the coil support tube 68 when fixed within the cylindrical base 64 and communicates with the at least first air slot 106 in the cylindrical base. In the example shown in FIGS. 9 and 13, the second air slot 134 is formed as a cutout notch with a notch positioned on either side of the coil support tube 68 to form opposing air slots and aligned with the opposing first air slots 106 on the cylindrical base 64. The heating coil 84 is received within the coil support tube 68 adjacent the openings 128 and extends vertically downward slightly, but does not extend below the lower section of the cylindrical base 64 and the first air slot 106. A cylindrical porous wick 86 surrounds the heating coil 84 and an electrical lead 140 connects the heating coil 84 and the contact pin 54 (FIGS. 13-15). Although a cylindrical porous wick 86 is illustrated, it may be different configurations.

This arrangement is advantageous because the electrical lead 140 is a thin wire connected between the heating coil 84 and the contact pin 54 and reduces airflow resistance of air that is drawn into the central air passage 126 and over the heating coil 84 and into the porous wick 86. In an example, the porous wick 86 is an organic cotton wick. It is also possible to use other materials but it has been found that an organic cotton wick works advantageously with botanical extracts such as derived from *cannabis* and other products, including THC components, cannabinoids, rosemary, garlic, dandelion, other greens and other health and nutrient rich botanical extracts. In an example, the heating coil 84 is a ceramic heating coil and in an example, a ceramic kanthal wire. It may also be a mesh coil in an example.

The tank cap 60 is received over the cylindrical base 64 and sealed thereto in a preferred permanent seal. An example is a snap-fit where the tank cap is formed is a closed cylindrical member and includes an internal notch 116 that receives in a snap-fit the circumferential and peripheral tab or shoulder formed on the outer surface 100 of the cylindrical base 64. A press fit or additional adhesive or other means could be used to help seal the tank cap 60 and provide a sealed fluid tank 71. The tank cap 60 encloses the coil support tube 68 as a shell forming the sealed fluid tank 71 for holding the vaping fluid, and more particularly, a botanical extract. The second O-ring 92 is positioned between the cylindrical base 64 and the tank cap 60 to prevent leakage of the vaping fluid, e.g., the botanical extract between the two members. The tank cap 60 has at least one third air slot 142 (FIGS. 1-3 and 13) formed at a level below the angled tank floor 102 and communicates with the at least first and second air slots 106, 134. In the example, opposing third air slots 142 are formed 180° apart on either side of the tank cap 60 and communicate with the opposing first and second air slots 106, 134 that are aligned with the third air slot.

As noted before, the tank cap 60 has its substantially planar upper surface 72 and the central vapor outlet 74 formed as an outlet tube 78 having its upper end extending from the upper surface and its lower end that connects to the upper end of the coil support tube 68. The configuration or diameter in this example of the lower end of the outlet tube 78 is configured to fit within the upper end of the coil support tube 68 in a sealed engagement. The upper end of the coil support tube 68 could be different configurations and shapes. When air is drawn in through the first, second and third air slots 106, 134 and 142 by vacuum, such as when a user draws on the upper end at the vapor outlet 74 via the drip tip 70, air is drawn through the at least first, second and third air slots upward into the coil support tube 68 through the cylindrical porous wick 86, thus drawing vaping fluid or the botanical extract contained within the sealed fluid tank 71 through the at least one opening 128 in the coil support tube into the cylindrical porous wick 86 for vaporization by the heating coil 84 and discharge from the outlet tube 78 within the tank cap 60. In this process, the angled tank floor 102 is configured to assist gravity feeding of the vaping fluid from the sealed fluid tank 71 to the porous wick adjacent the heating coil to transfer heat to the vaping fluid or botanical extract.

As noted before, preferably four openings 128 are illustrated and positioned in the illustrated example about 90° apart from each other. The diameter of the openings may vary depending on the viscosity of the vaping fluid or botanical extract. A more viscous vaping fluid or botanical extract may require a larger diameter opening 128 to aid in passing from the sealed fluid tank 71 into the porous wick 86. For example, the openings could range in diameter from about 0.5 mm up to about 5.0 mm. Representative examples of different sized openings include 1.5 mm, 1.8 mm, 2.0 mm, 2.5 mm, and 3.0 mm. Users may select different vaporizers 50 having different sized diameter openings 128 depending on their selected vaping fluid or botanical extract and its viscosity.

Figure 10:
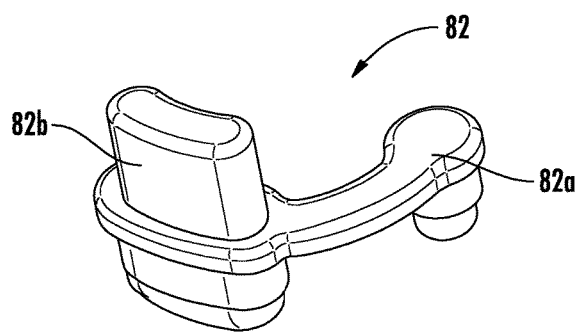
FIG. 10 is an isometric view of the plug shown in FIG. 4.

The sealed fluid tank 71 is filled initially, preferably one time only when a botanical extract is used and the drip tip is permanently sealed, through the fill hole 80 filling the sealed fluid tank with the vapor fluid or botanical extract. The plug 82 is secured into the fill hole. The plug 82 as shown in FIG. 10 is a rubber plug that includes a shoulder extension 82a that retains the plug onto the tank cap 60 and the enlarged plug section 82b with a grip extending upward from the plug and bottom section, which is secured within the fill hole.

Figure 11:
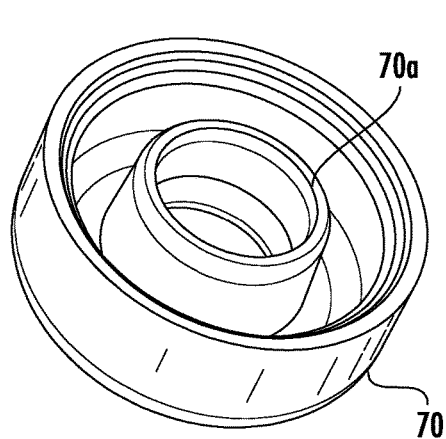
FIG. 11 is a bottom isometric view of the drip tip shown in FIG. 5.
Figure 12:
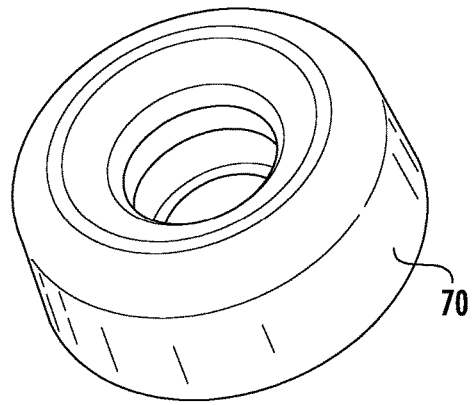
FIG. 12 is a top isometric view of the drip tip shown in FIG. 5.

As best illustrated in FIGS. 13-15, the drip tip 70 is secured onto the tank cap 60 and covers the plug 82. In an example, the drip tip 70 is secured onto the tank cap 60 so that it cannot be removed, and thus, forming in an example a single use, disposable vaporizer 50 that operates as a vaporizer and aromatherapy diffuser for expensive botanical extracts. The vaporizer 50 may be discarded once all the botanical extract has been drawn into the wick 86 and the sealed fluid tank 71 is empty. The drip tip 70 may be permanently secured onto the tank cap 60 by different means, including, but not limited to, a snap-on, spin weld, adhesive bond or press fit securement so that it is retained and cannot be removed by a user, thus forming a single use, disposable vaporizer 50. The drip tip 70 as shown in the example of FIGS. 11 and 12 includes a central cylindrical post 70a that forms an internal annular ring that is received onto the outlet tube 78 at its upper end and also receives the upper enlarged section of the plug 82 that is dimensioned at its upper portion that can be grasped by a user for initial filling to fit within and be covered by the drip tip as best shown in FIGS. 13-15. In an example, the cylindrical post 70a of the drip tip 70 is configured to aid retention onto the upper end of the outlet tube 78 via a snap-fit groove in some examples as shown in FIG. 4.

As noted before, the angled tank floor 102 is configured to assist gravity feeding of a viscous vaping fluid such as the more viscous botanical extract from the sealed fluid tank 71 to the porous wick 86 and ensure vaping fluid is readily transferred adjacent to the heating coil 84 and help transfer heat to the botanical extract and thin it. When the sealed fluid tank 71 is filled with the vaping fluid, it preferably creates a low pressure air pocket that retains the vaping fluid within the sealed fluid tank 71 until a user draws air through the central air passage formed by the upper end of the coil support tube 68 and outlet tube of the tank cap 60 to allow vaping fluid to flow into the porous wick 86 and central air passage. Drawing air creates a lower air pressure than the lower pressure air pocket in the sealed fluid tank 71.

In an example, the sealed fluid tank 71 may vary in its capacity depending on the dimensions used to manufacture the different components, but in one example has a capacity of 0.3 milliliters to 8.0 milliliters, and in one preferred embodiment, is about 1.0 to 5.0 milliliters and examples may include a sealed fluid tank 71 having 2.0 milliliter capacity and in another example 4.0 milliliters capacity. Because of the use of the botanical extracts, the heating coil 84 is preferably a ceramic heating coil, and more particularly, a ceramic kanthal heating coil having a resistance ranging from 0.11 to 2.10 ohms, and in one example, a sub ohm heating coil of about 0.60 ohms. The device may operate at about 10 to about 100 watts, and in another example, about 30 to about 70 watts.

The fully sealed fluid tank 71 prevents spills and unnecessary user exposure to the vaping fluid or botanical extract. The fully sealed fluid tank 71 also prevents premature oxidation and spoiling of expensive vaping fluid such as formed from botanical extracts, including *cannabis* products. The drip tip 70 that is retained permanently by different means, such as by snap-on, spin welding, adhesive bonding or press fit, as non-limiting examples, serves as a secondary closure for the plug 82. The trapped air pocket that is created by the sealed fluid tank 71 as a fluid reservoir creates a low pressure pocket that retains the vaping fluid or botanical extract within the fluid tank until the user induces what is in an example a Bernoulli effect by drawing air through the central air passage, creating a lower pressure in the air passage than the pressure in the trapped air pocket to draw the fluid out into the porous wick material.

The angled tank floor 102 ensures that the gravity assisted feeding of the vaping fluid such as the botanical extract to the porous wick 86 will ensure that every drop of vaping fluid or botanical extract travels to the porous wick to be heated and vaporized and ensures that the porous wick is properly wetted during use. With this design, more vaping fluid such as the botanical extract is moved close to the heat source, i.e., the heating coil 84 as possible, to transfer heat from the heating coil 84 to the vaping fluid or botanical extract, thereby thinning the vaping fluid and especially a botanical extract in its preferred use, for better flow and feeding of the botanical extract to the porous wick 86. The heating coil 84 should be understood to also refer to a mesh heating element and not necessarily formed as a standard coil, but still considered a heating coil. The use of the ceramic resistive heating element as a heating coil allows heating to a proper temperature and the electrical lead 140 or wire connection from the heating coil 84 to the contact pin 54 minimizes the material in the air flow path to allow for larger, unrestricted air flow into the porous wick and heating coil. Use of inexpensive injection molded plastics for the primary components as described above allows for lower unit per unit cost and permits a better single use disposable product whereas the traditional metal assemblies and glass assemblies are cost prohibitive. The 510 connection as the threaded connector 52 is integrated into the vaporizer 50 and allows the integration with existing vapor products and battery housings already widely used in the market.

Figure 16:
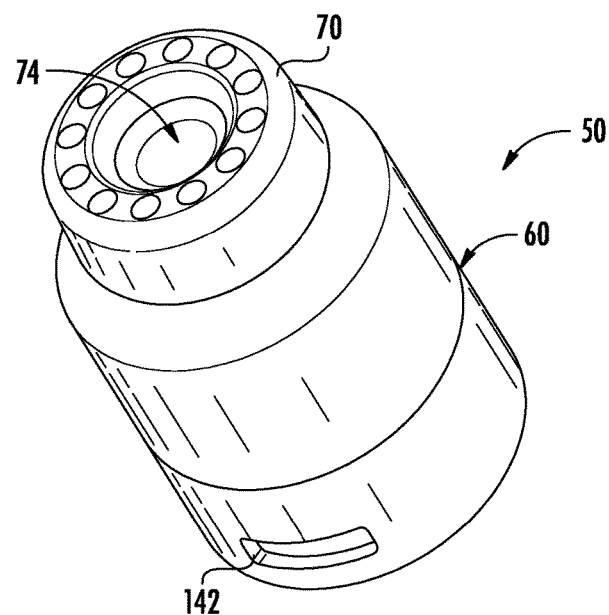
FIG. 16 is an isometric view of another aspect of the vaporizer.
Figure 17:
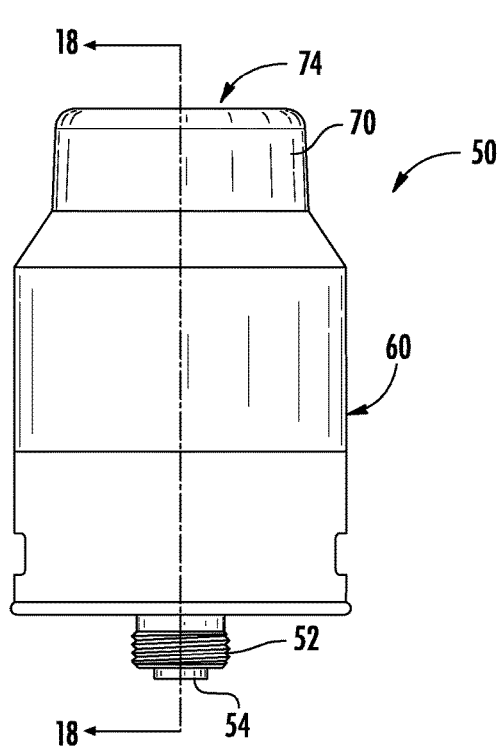
FIG. 17 is a side elevation view of the vaporizer shown in FIG. 16.
Figure 18:
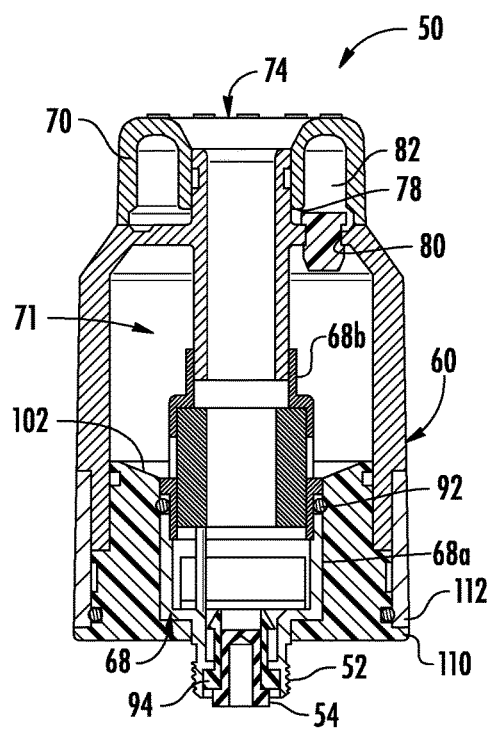
FIG. 18 is a sectional view of the vaporizer taken along line 18-18 of FIG. 17.

The example of the vaporizer shown in FIGS. 1-15 has about a 2 milliliter fluid tank. A second aspect of the vaporizer 50 is shown in FIGS. 16-18 where the sealed fluid tank is slightly larger at 4 milliliters and the tank cap 60 is formed in multiple sections, and as illustrated, as an upper section 60a and a lower section 60b, which retains the upper section against the cylindrical base 64 as shown in the sectional view of FIG. 18. This lower section may contain the third air slot 142 as illustrated. The lower section may snap-fit onto the cylindrical base. The upper section of the cylindrical base may include a circumferential slot having a reduced diameter than the lower section so that a lower extension of the tank cap is received within a peripheral or annular groove formed between the lower section and the cylindrical base. A different type of heating element as a heating coil may be used in this example as a mesh element or mesh coil instead of a ceramic coil as in the example of FIGS. 1-15. The coil support tube 68 may also be formed of multiple sections, including lower and upper tube sections 68a, 68b. The sealed tank 71 is vertically higher than that illustrated in FIGS. 1-15, allowing a 4 millimeter capacity instead of 2 millimeter capacity. The tank size can vary. Otherwise the components are substantially the same except for minor decorative features.

The kanthal ceramic coil is preferred for use with botanical extracts, but different types of heating coils "vape wires" may be used, including Kanthal (FeCrAl) derivatives, Nichrome, stainless steel, nickel, and titanium. Stainless steel is considered by many to be the most versatile. Different grades of stainless steel wire may be used. The most popular gauges for the wire are 32, 30, 28, 26, 24, and 22. The type of wicking material can vary and preferably includes the organic cotton for the use with botanical extracts, but in some cases, Japanese cotton pads, ekowool, silica, and rayon fiber may possibly be used.

Figure 19:
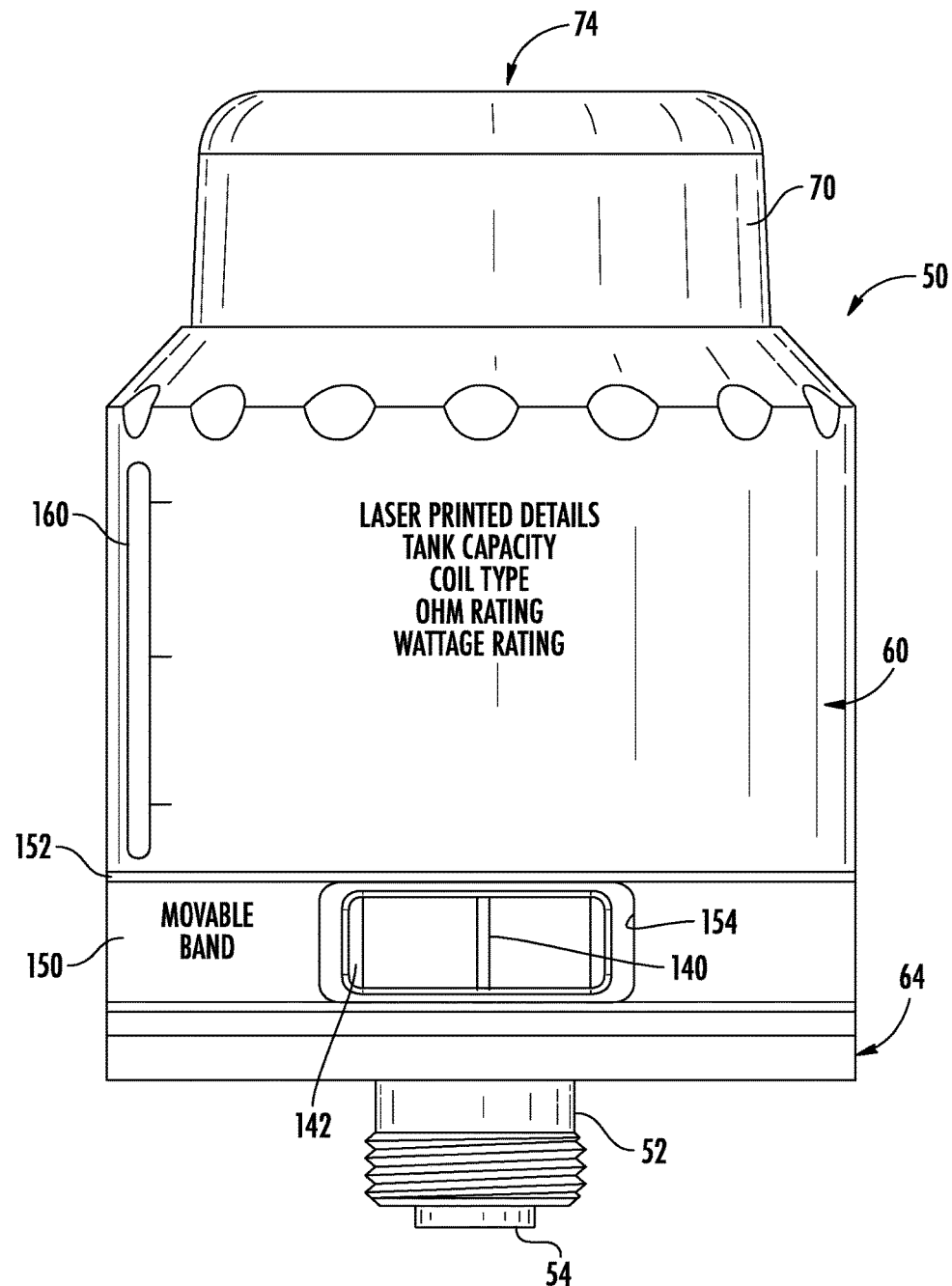
FIG. 19 is a front elevation view of the vaporizer of FIG. 3 showing additional details and a slidable ring that regulates air flow.

Referring now to FIG. 19, another aspect of the vaporizer 50 is shown. A moveable band or collar 150, such as a circumferential band slidable in a circumferential slot 152 formed on the periphery of the tank cap 60, is slidable over the third air slot 142. The band or collar 150 includes an opening 154 that can be slid over the third air slot 142 and acts to regulate the amount of air that can be drawn inward through the vaporizer. Details of the vaporizer 50 may be laser printed onto the side of the tank cap 60 to help identify the type of components. This information could include the fluid tank capacity, the type of heating coil, the ohm rating of the heating coil, and wattage rating to determine a preferred range. Other details could include the nature of the vaping fluid or botanical extract contained within the fluid tank 71, especially relevant when the fluid tank is permanently sealed. It is also possible to include a level indicator 160 that may give a fill line or indication of how much vaping fluid or botanical extract remains in the fluid tank 71. It could be advantageous to know for sure the vaporizer 50 may be discarded when it is a sealed fluid tank 71 or how much vaping fluid or botanical extract is left, and thus, another vaporizer 71 must be reordered, especially if the fluid tank is sealed, such as with a botanical extract that must be reordered when used for medicinal purposes.

The components forming the vaporizer may have different dimensions, but typically may range in size by up to about 20% to 30% of an average size. For example, the tank cap 60 can vary in size and average about 24 mm in diameter and range from about 15 mm to about 30 mm and have a vertical height from about 20 mm to 50 mm, depending on the capacity of the sealed tank 71. Other sizes are possible. The drip tip is usually about 18.5 mm average in diameter, but can range in size from about 10 mm to 25 mm, and can be different configurations. Other sizes are possible.

The cylindrical base 64 can average about 24 mm diameter at the ridge 110 and about 22.0 mm at the outer surface 100. These values can vary up to 20% to 40% in some examples or more. The coil support tube 68 can average about 10.5 mm diameter at the upper section and its air slots could be about 0.5 to 5.0 mm. The vertical height from the connector to the uppermost section could be about 20 mm as an average. The openings in its side could be about 0.5 mm to 5.0 mm diameter as noted before. The air slots are typically rectangular configured as illustrated, but could be many different configurations.

These are all example dimensions only and can vary as determined by those skilled in the art based on fluid tank capacity, the types of heating coils, wicks, and other design features.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that the modifications and embodiments are intended to be included within the scope of the dependent claims.

That which is claimed is:

1. A vaporizer and aromatherapy diffuser, comprising:
a base having an outer surface and conical upper surface defining an angled tank floor, said base having a central orifice and at least one first air slot extending from the outer surface into the central orifice below the angled tank floor;
a coil support tube received within the central orifice of the base and having a lower end extending below the base and configured as a connector to connect to a battery housing and a contact pin carried at the connector, and an upper end extending above the base and forming a central air passage, said coil support tube having at least one opening formed in the side adjacent the angled tank floor and at least a second air slot below the angled tank floor and communicating with the at least first air slot in said base;
a heating coil received within the coil support tube adjacent the at least one opening, and a porous wick surrounding the heating coil;
a lead connecting the heating coil and the contact pin;
a tank cap received over the base and sealed thereto and enclosing the coil support tube as a shell forming a sealed fluid tank for holding vaping fluid, said tank cap having at least one third air slot formed below the angled tank floor and communicating with the at least one first and second air slots, said tank cap having an upper surface and a central vapor outlet having an upper end extending from the upper surface and a lower end that connects to the upper end of the coil support tube in sealed engagement, wherein upon suction applied at the upper end of the outlet, air is drawn through the at least first, second and third air slots upward into the coil support tube through the porous wick and drawing vaping fluid contained within the sealed fluid tank through the at least one opening in the coil support tube into the porous wick for vaporization by said heating coil and discharge from the outlet within the tank cap, said tank cap having a fill hole within the upper surface to allow filling of said sealed fluid tank with a vaping fluid and a plug secured into said fill hole; and a drip tip secured onto the tank cap and covering the plug.

2. The vaporizer and aromatherapy diffuser according to claim 1, wherein said vaping fluid comprises a botanical extract.

3. The vaporizer and aromatherapy diffuser according to claim 1, wherein said angled tank floor is configured to assist gravity feeding of said vaping fluid from the sealed tank to the porous wick and adjacent the heating coil to transfer heat to the vaping fluid.

4. The vaporizer and aromatherapy diffuser according to claim 1, wherein said drip tip is secured onto the tank cap and covers said plug secured within the fill hole to prevent refill of said sealed fluid tank with a vaping fluid.

5. The vaporizer and aromatherapy diffuser according to claim 1, wherein said heating coil comprises a ceramic heating coil.

6. The vaporizer and aromatherapy diffuser according to claim 1, wherein said heating coil comprises a mesh heating coil.

7. The vaporizer and aromatherapy diffuser according to claim 1, wherein said porous wick comprises a cotton wick.

8. The vaporizer and aromatherapy diffuser according to claim 1, wherein said sealed fluid tank has a capacity of 0.3 milliliters to 8.0 milliliters.

9. The vaporizer and aromatherapy diffuser according to claim 1, wherein said heating coil has a 0.11 ohm to 2.1 ohm resistance.

10. The vaporizer and aromatherapy diffuser according to claim 1, wherein said base, coil support tube, tank cap and drip tip cap are formed of a plastic material.

11. The vaporizer and aromatherapy diffuser according to claim 1, wherein said connector at the lower end of said coil support tube comprises a 510 connector to connect to a battery housing of a vaping mod device.

12. The vaporizer and aromatherapy diffuser according to claim 1, further comprising an O-ring between said base and tank cap to prevent leakage of vaping fluid therebetween.

13. The vaporizer and aromatherapy diffuser according to claim 1, further comprising an O-ring between said base and coil support tube to prevent leakage of vaping fluid therebetween.

14. The vaporizer and aromatherapy diffuser according to claim 1, wherein said sealed fluid tank when filled with a vaping fluid creates a low pressure air pocket that retains the vaping fluid within the sealed fluid tank until a user draws air through the central passage formed by said upper end of the coil support tube and outlet of said tank cap to create a lower air pressure in the central passage than in the sealed fluid tank and allow vaping fluid to flow into the porous wick and central air passage.

15. The vaporizer and aromatherapy diffuser according to claim 1, wherein said drip tip comprises a permanent securement onto the tank cap.

16. The vaporizer and aromatherapy diffuser according to claim 1, wherein said tank cap comprises multiple sections, including an upper section and a lower section, wherein the upper section retains the upper section against the base.

17. The vaporizer and aromatherapy diffuser according to claim 1, wherein the coil support tube comprises multiple sections, including upper and lower sections.

18. A single use, disposable vaporizer and aromatherapy diffuser for botanical extracts, comprising:

a cylindrical base having an outer surface and conical upper surface defining an angled tank floor, said cylindrical base having a central orifice and at least one first air slot extending from the outer surface into the central orifice below the angled tank floor;

a coil support tube received within the central orifice of the cylindrical base and having a lower end extending below the cylindrical base and configured as a connector to connect to a battery housing and a contact pin carried at the connector, and an upper end extending above the cylindrical base and forming a central air passage, said coil support tube having at least one opening formed in the side adjacent the angled tank floor and at least a second air slot below the angled tank floor and communicating with the at least first air slot in said cylindrical base;

a 0.11 ohm to 2.1 ohm resistance ceramic or mesh heating coil received within the coil support tube adjacent the at least one opening, and a porous wick surrounding the ceramic or mesh heating coil;

a lead connecting the ceramic or mesh heating coil and the contact pin;

a tank cap received over the cylindrical base and permanently sealed thereto and enclosing the coil support tube as a shell forming a sealed fluid tank having a capacity of 0.3 milliliters to 8.0 milliliters for holding the botanical extract, said tank cap having at least one third air slot formed below the angled tank floor and communicating with the at least one first and second air slots, said tank cap having an upper surface and a central vapor outlet formed as an outlet tube having an upper end extending from the upper surface and a lower end that connects to the upper end of the coil support tube in sealed engagement, wherein upon suction applied at the upper end of the outlet tube, air is drawn through the at least first, second and third air slots upward into the coil support tube through the porous wick and drawing botanical extract contained within the sealed fluid tank through the at least one opening in the coil support tube into the porous wick for vaporization of the botanical extract by said ceramic or mesh heating coil and discharge from the outlet tube within the tank cap, said tank cap having a fill hole within the upper surface to allow filling of said sealed fluid tank with a botanical extract and a plug secured into said fill hole; and a drip tip secured onto the tank cap and being unremovable by a user and covering the plug secured within the fill hole to prevent removal of the plug and refill of the sealed fluid tank with a botanical extract.

19. The single use, disposable vaporizer and aromatherapy diffuser according to claim 18, wherein said angled tank floor is configured to assist gravity feeding of said botanical extract from the sealed fluid tank to the porous wick and adjacent the ceramic or mesh heating coil to transfer heat to the botanical extract and thin the botanical extract.

20. The single use, disposable vaporizer and aromatherapy diffuser according to claim 18, wherein said cylindrical base, coil support tube, tank cap and drip tip cap are formed of a plastic material.

21. The single use, disposable vaporizer and aromatherapy diffuser according to claim 18, wherein said connector at the lower end of said coil support tube comprises a 510 connector to connect to a battery housing of a vaping mod device.

22. The single use, disposable vaporizer and aromatherapy diffuser according to claim 18, further comprising an O-ring positioned between said cylindrical base and tank cap to prevent leakage of botanical extract therebetween.

23. The single use, disposable vaporizer and aromatherapy diffuser according to claim 18, further comprising an O-ring positioned between said cylindrical base and coil support tube to prevent leakage of botanical extract therebetween.

24. The single use, disposable vaporizer and aromatherapy diffuser according to claim 18, wherein said sealed fluid tank when filled with a botanical extract creates a low pressure air pocket that retains the botanical extract within the fluid tank until a user draws air through the central passage formed by said upper end of the coil support tube and outlet tube of said tank cap to create a lower air pressure in the central passage than in the sealed fluid tank and allow botanical extract to flow into the porous wick and central air passage.

25. The single use, disposable vaporizer and aromatherapy diffuser according to claim 18, wherein said drip tip comprises permanent securement onto the tank cap.

26. The single use, disposable vaporizer and aromatherapy diffuser according to claim 18, wherein the tank cap comprises multiple sections, including an upper section and a lower section, wherein the lower section retains the upper section against the cylindrical base, said lower section having the at least one third air slot.

27. The single use, disposable vaporizer and aromatherapy diffuser according to claim 18, wherein the coil support tube comprises multiple sections, including an upper and lower section.

* * * * *